US012690833B2

(12) United States Patent
Prevrhal et al.

(10) Patent No.: US 12,690,833 B2
(45) Date of Patent: Jul. 28, 2026

(54) METHOD FOR PROVDING FEEDBACK DATA IN A MEDICAL IMAGING SYSTEM

(71) Applicant: KONINKLIJKE PHILIPS N.V., Eindhoven (NL)

(72) Inventors: Sven Peter Prevrhal, Hamburg (DE); Thomas Buelow, Grosshansdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 240 days.

(21) Appl. No.: 18/561,312

(22) PCT Filed: May 9, 2022

(86) PCT No.: PCT/EP2022/062388
§ 371 (c)(1),
(2) Date: Nov. 16, 2023

(87) PCT Pub. No.: WO2022/243073
PCT Pub. Date: Nov. 24, 2022

(65) Prior Publication Data
US 2024/0366177 A1     Nov. 7, 2024

(30) Foreign Application Priority Data

May 18, 2021     (EP) ..................................... 21174252

(51) Int. Cl.
*G06T 7/00* (2017.01)
*A61B 6/04* (2006.01)
(Continued)

(52) U.S. Cl.
CPC ................ *A61B 6/589* (2013.01); *A61B 6/04* (2013.01); *A61B 6/08* (2013.01); *G06T 7/0012* (2013.01);
(Continued)

(58) Field of Classification Search
CPC .. A61B 6/589; A61B 6/04; A61B 6/08; A61B 6/54; G06T 7/0012; G06T 7/75;
(Continued)

(56) References Cited

U.S. PATENT DOCUMENTS 6,490,475 B1    12/2002  Seeley
7,343,189 B2     3/2008  Kagermeier
(Continued)

FOREIGN PATENT DOCUMENTS

CN          104000588 A      8/2014
CN          205849464 U      1/2017
(Continued)

OTHER PUBLICATIONS

PCT International Search Report, International application No. PCT/EP2022/062388, Aug. 22, 2022.

*Primary Examiner* — Van D Huynh
(74) *Attorney, Agent, or Firm* — Larry Liberchuk

(57) ABSTRACT

A method for providing feedback data in a medical imaging system (22) for a medical imaging process, comprising the steps of: providing, by a calculation unit, a simulation model, trained to predict an appearance of a medical image to be acquired by using the medical imaging system (22) from a relation between subject positioning data associated with a captured positioning of a subject (27), equipment positioning data associated with a captured positioning of at least one medical care and/or monitoring equipment (28, 30) arranged in or at the subject (27) in a medical imaging system (22), and medical image data associated with the subject positioning data and the medical care and/or monitoring equipment positioning data (S10); obtaining, by the calculation unit, from at least one measuring means (25, 26), current subject positioning data of a subject (27) and current medical equipment positioning data of at least one medical care and/or monitoring equipment (28, 30) arranged in or at
(Continued)

the subject (27) in the medical imaging system (S20); determining, by the calculation unit, feedback data by feeding the obtained current subject positioning data and the obtained current medical equipment positioning data into the simulation model outputting the feedback data, wherein the feedback data comprise at least simulated medical image data predicted by the simulation model from the obtained current subject positioning data and current medical equipment positioning data (S30); providing, by a provision unit, the feedback data (S40).

12 Claims, 1 Drawing Sheet

(51) Int. Cl.

| | |
|---|---|
| *A61B 6/08* | (2006.01) |
| *A61B 6/58* | (2024.01) |
| *G06T 7/73* | (2017.01) |
| *G16H 30/40* | (2018.01) |

(52) U.S. Cl.
CPC ............... *G06T 7/75* (2017.01); *G16H 30/40* (2018.01); *G06T 2207/10116* (2013.01); *G06T 2207/20081* (2013.01); *G06T 2207/20084* (2013.01)

(58) Field of Classification Search
CPC . G06T 2207/10116; G06T 2207/20081; G06T 2207/20084; G16H 30/40; G16H 40/40
See application file for complete search history.

(56) References Cited

U.S. PATENT DOCUMENTS

| | | | | |
|---|---|---|---|---|
| 9,235,973 | B2 | 1/2016 | Popescu | |
| 10,825,251 | B2 | 11/2020 | Peltola | |
| 11,000,336 | B2 | 5/2021 | Harks | |
| 2003/0088179 | A1 | 5/2003 | Seeley | |
| 2006/0274145 | A1* | 12/2006 | Reiner | G16H 30/20 |
| | | | | 707/E17.031 |
| 2008/0037708 | A1 | 2/2008 | Kuzmanovic | |
| 2009/0107658 | A1 | 4/2009 | Takewaka | |
| 2010/0167248 | A1* | 7/2010 | Ryan | H04N 7/181 |
| | | | | 434/262 |
| 2010/0322375 | A1 | 12/2010 | Hirokawa | |
| 2011/0236868 | A1* | 9/2011 | Bronstein | G09B 23/30 |
| | | | | 434/267 |
| 2013/0121556 | A1* | 5/2013 | Matsumoto | G06T 7/0012 |
| | | | | 382/132 |
| 2015/0228071 | A1 | 8/2015 | Jockel | |
| 2016/0213329 | A1 | 7/2016 | Dirkes | |
| 2018/0158209 | A1* | 6/2018 | Fine | G06N 20/00 |
| 2018/0232872 | A1 | 8/2018 | Katsumata | |
| 2019/0000564 | A1 | 1/2019 | Navab | |
| 2020/0008772 | A1* | 1/2020 | Ghamari | A61B 6/583 |
| 2020/0268349 | A1* | 8/2020 | Buras | G06N 20/00 |
| 2024/0081784 | A1* | 3/2024 | Nikou | A61B 8/085 |
| 2025/0295469 | A1* | 9/2025 | Quist | A61B 34/10 |
| 2025/0311996 | A1* | 10/2025 | Sun | A61B 6/488 |

FOREIGN PATENT DOCUMENTS

| | | | |
|---|---|---|---|
| EP | 1278458 | A2 | 1/2003 |
| EP | 3453330 | A1 | 3/2019 |
| JP | 2013102850 | A | 5/2013 |

* cited by examiner

METHOD FOR PROVDING FEEDBACK DATA IN A MEDICAL IMAGING SYSTEM

FIELD OF THE INVENTION

The invention relates to a method for providing feedback data in a medical imaging system for a medical imaging process, an apparatus for providing feedback data in a medical imaging system for a medical imaging process, a system, a use of an optical measuring unit and/or a pressure based measuring unit in such an apparatus, and a computer program element.

BACKGROUND OF THE INVENTION

Medical imaging is an important issue in medical diagnostics. There are several medical imaging systems available on the market, such as X-ray, MRT, CT etc. These medical imaging systems are state of the art and therefore known. The quality of the medical image obtained by such medical imaging systems depends among others on the quality of the preparation of the medical imaging process. In case the quality of the medical image is insufficient, medical imaging has to be repeated or even worse, a wrong medical diagnosis may be derived from the medical image. In sum, this may lead to increased costs for medical imaging, wrong medical diagnosis, and to a reduced image quality.

SUMMARY OF THE INVENTION

There may, therefore, be a need for providing feedback in medical imaging, in particular in the preparation phase of medical imaging. The object of the present invention is solved by the subject matter of the independent claims, wherein further embodiments are incorporated in the dependent claims.

According to a first aspect, a method for providing feedback data in a medical imaging system for a medical imaging process is provided. The method comprises the steps of:

Providing, by a calculation unit, a simulation model, trained to describe a relation between positioning data of a subject and of at least one medical equipment arranged to the subject in a medical imaging system and simulated image data resulting from the positioning data. Obtaining, by the calculation unit, from at least one measuring means, positioning data of a subject and of at least one medical equipment arranged to the subject in the medical imaging system. Determining, by the calculation unit, feedback data by utilizing the simulation model and the obtained positioning data fed into the simulation model, wherein the feedback data comprise at least simulated image data resulting from the obtained positioning data. Providing, by a provision unit, the feedback data.

In other words, the method comprises the steps of providing, by a calculation unit, a simulation model, trained to predict an appearance of a medical image to be acquired by using the medical imaging system from a relation between subject positioning data associated with a captured positioning of a subject, medical equipment positioning data associated with a captured positioning of at least one medical care and/or monitoring equipment arranged in or at the subject in a medical imaging system, and medical image data, optionally simulated medical image data, associated with the subject positioning data and the medical equipment positioning data; obtaining, by the calculation unit, from at least one measuring means, current subject positioning data of a subject and current equipment positioning data of at least one medical care and/or monitoring equipment arranged in or at the subject in the medical imaging system; determining, by the calculation unit, feedback data by feeding the obtained current subject positioning data and the obtained current medical equipment positioning data into the simulation model for processing, wherein the feedback data comprise at least simulated medical image data predicted by the simulation model from at least the obtained current subject positioning data and current medical equipment positioning data; and providing, by a provision unit, the feedback data.

The term feedback data, as used herein, is to be understood broadly and relates to any information configured to describe the medical imaging process. The feedback data may consider any phase of the medical imaging process, such as preparation phase, in which, for example, a subject is prepared before the actual image acquisition phase, execution phase or acquisition phase, and follow-up phase. The feedback data may comprise quality measures concerning the medical imaging process that reveal whether the medical imaging process is under the actual settings (i.e. positioning data, exposure data etc.) leading to a medical image with a sufficient quality, particularly image quality, or an insufficient quality. The feedback data may comprise a process parameter describing a medical imaging process (e.g. positioning data, a medical imaging system setting). In at least some embodiments, the feedback data may comprise a prediction of an image, particularly medical image, such as an X-ray image, MR image data, CT image data, or the like, that would be obtained by actual imaging conditions (e.g. medical imaging system setting, positioning data, and type or class of medical care and/or monitoring equipment). The feedback data may comprise simulated image data.

The term medical imaging system, as used herein, is to be understood broadly and relates to any medical imaging system configured to acquire a medical image of a subject. The medical imaging system may be an X-ray system, a MRT system or a CT system. The medical imaging system may comprise a medical imaging unit, a control unit, a support structure configured to position a subject to be imaged (e.g. a bed), a display configured to display information (e.g. feedback data), and/or a measurement means.

The term calculation unit, as used herein, is to be understood broadly and relates to a system configured to execute a simulation model. The calculation unit may be a hardware unit (e.g. CPU, workstation etc.) or a virtual unit (e.g. virtual machine, a software etc.).

The term simulation model, as used herein, is to be understood broadly and relates to any computational model configured to be trained, by e.g. corresponding training data etc., to describe at least a relation, particularly relationship, between subject positioning data of a subject, of a medical care and/or monitoring equipment and corresponding, optionally simulated, medical image data. The simulation model may be based on a neural network, a deep learning algorithm or, more generally, a machine-learning algorithm. The simulation model may be trained by providing measured positioning data as input and a corresponding actual acquired image, particularly medical image, of the subject at the same time as output. The training data may optionally be annotated, labeled or the like. The simulation model may be continuously trained or re-trained, respectively. The simulation model may be used to predict an appearance of an image, particularly medical image, such as an X-ray image, MR image or the like, that would be acquired under the given imaging conditions. The simulation model may be an entity that processes one or more inputs into one or more outputs by means of an internal processing chain that typically has a set of free parameters. The internal processing chain may be organized in interconnected layers that are traversed consecutively when proceeding from the input to the output. The input may be in the present case positioning data of the subject, the medical care and/or monitoring equipment, the medical imaging system, and exposure data and the output may be a simulated medical image. The simulation model may be trained using records of training data. A record of training data comprises training input data and corresponding training output data. The training output data of a record of training data is the result that is expected to be produced by the simulation model when being given the training input data of the same record of training data as input. The deviation between this expected result and the actual result produced by the simulation model is observed and rated by means of a "loss function". This loss function is used as a feedback for adjusting the parameters of the internal processing chain of the module. For example, the parameters may be adjusted with the optimization goal of minimizing the values of the loss function that result when all training input data is fed into the module and the outcome is compared with the corresponding training output data. The result of this training is that given a relatively small number of records of training data as "ground truth", the simulation model is enabled to perform its job, in the present case to provide feedback data, in particular simulated medical images.

The term positioning data means in the present case spatial data of one or more center points (i.e. skeletal joint centers or key points) of the subject and/or the medical care and/or monitoring equipment and spatial data of one or more outline points of the subject and/or the medical care and/or monitoring equipment. The positioning data may be preferably in relation to a coordinate system of the medical imaging system.

The term subject, as used herein, is to be understood broadly and relates to any part of a human or animal. The subject may comprise be bone (e.g. knee), tissue and/or an organ (e.g. heart, brain).

The term medical care and/or monitoring equipment, as used herein, is to be understood broadly and relates to any equipment which is configured to provide medical aid (e.g. tube, lines etc.) to the subject or to be used for medical imaging (e.g. support structure to position a part of the subject: medical weight or a medical spreading device). For example, the medical care and/or monitoring equipment may be configured to be brought directly to the subject, for example contacting the subject or being at least partially inserted into the subject. The medical care and/or monitoring equipment can be used to provide the medical aid, such as a medication, an infusion, oxygen, etc. to the subject, and/or to monitor vital parameters of the subject, such as heart rate measurement, oxygen measurement, etc. The medical care and/or monitoring equipment may interfere with the beam path during image acquisition due to its material and/or position relative to the subject and/or the medical imaging system.

The term measuring means, as used herein, is to be understood broadly and relates to any means configured to determine positioning data of the subject and/or the medical care and/or monitoring equipment. The term measuring means may comprise an optical measuring unit, a tactile measuring unit, a pressure based measuring unit, an imaging system internal measuring unit (e.g. encoder of a drive of the medical imaging system).

The term simulated image data, as used herein, means a simulation of an image that would be acquired with a medical imaging system under measured imaging settings. The simulated image may be essentially the same as the real image acquired without specific characteristics of the subject (e.g. an unknown tumor, a deviation of normal bone structure etc.). It should be noted that simulated image data does not replace the real obtained medical image of the subject, instead the simulated image should assist a technologist to recognize whether the imaging settings are appropriate to obtain a reasonable medical image of the subject in reality.

The invention is based on the finding that the quality of a medical image is crucial for follow-up diagnosis of the medical image. E.g. in X-ray imaging positioning, the subject or the medical care and/or monitoring equipment for an optimal diagnostic value of the resulting image poses a serious challenge. For instance, bedside chest x-ray (CXR) is an indispensable diagnostic tool for monitoring seriously ill patients in the intensive care unit (ICU). The CXR often reveals abnormalities that may not be detected clinically. In addition, bedside CXRs are an irreplaceable tool to detect the malposition of tubes and lines and to identify associated complications. Another example is chest x-ray screening, where again it is often difficult to assess position and spatial extent of the lungs. Another example is breast imaging, where it is often difficult to achieve a full view extending to the chest wall.

There are many factors influencing the quality of a medical image, such as positioning data of a subject and/or medical care and/or monitoring equipment and the medical imaging system, in particular an alignment to each other of the subject, the medical care and/or monitoring equipment and the medical imaging system. E.g. the position of mandatory medical care and/or monitoring equipment (e.g. breathing tube, infusion tube, or the like) might have, due to its material and/or position relative to the subject and/or the medical imaging system, negative influence on the quality of the medical image (e.g. the medical care and/or monitoring equipment hides an organ or it is unclear in the resulting image what part of the medical image belongs to the subject and what to the medical care and/or monitoring equipment) and should therefore be adjusted. The medical care and/or monitoring equipment may be mandatory as the subject is in a bed in an intensive care unit (ICU). It is crucial for diagnosis to know whether the medical care and/or monitoring equipment is inside the subject or outside the subject. A technician preparing a medical imaging process of the subject, therefore, has a significant influence to influence the quality of the medical image by adjusting the positioning data of the medical imaging system. In order to assess the influence of the positioning data, the provision of feedback data to the technician, in particular a simulated image resulting from the positioning data is crucial. Based on the feedback data in form of the simulated image the technician can see and assess directly whether the image quality could be sufficient with the current positioning data and/or whether an adjustment of the current positioning data might be necessary. This may advantageously increase the image quality and the efficiency of the medical imaging process, as fewer repetitions are necessary due to avoidance of images with insufficient image quality. Furthermore, in case of an X-ray imaging, a subject may advantageously receive only little X-ray dose as no repetitions of medical imaging are necessary.

In other words, the method as described herein proposes to provide a technician with feedback, in particular a visual feedback, on current subject and/or equipment positioning.

It does so by simulating a medical image, e.g. an X-ray image that would result if the medical image were taken under current situation. Thereby, the method may be carried out radiation free, i.e. without using the actual medical imaging system. The technician can infer from the simulated medical image whether the subject, in particular an anatomy of interest, would be optimally imaged by the medical imaging system, i.e. fully, in the optimal position, correctly exposed and e.g. without overlapping x-ray shadows from medical care and/or monitoring equipment. The simulated medical image may be generated by a software processor that uses input measuring means such as a video camera, a pressure sensor for the subject's position and/or the medical care and/or monitoring equipment's position, input from the medical image system about exposure settings (e.g. position of source, detector etc.), and catalogued knowledge of medical image characteristics of medical care and/or monitoring equipment. The catalogued knowledge may show e.g. how an X-ray image would look like if a medical care and/or monitoring equipment, e.g. a venous line, has a specific position and size. The medical care and/or monitoring equipment inside/outside of patient confusion is also alleviated by the method, as a medical care and/or monitoring equipment outside the patient are picked up by the camera sensors and can be labelled as such on the simulated x-ray image. The radiologist reader can then simply compare the labelled simulated image with the actual x-ray imaging they are reading.

According to an embodiment, the medical care and/or monitoring equipment may comprise one or more medical care means configured to provide a medical care to the subject. Medical care, as used herein, means a supply of substances (e.g. saline solutions, oxygen) or an observation of health function (e.g. measurement electrodes). The medical care and/or monitoring equipment may be vital for the subject and therefore cannot be removed from the subject. Hence, it may be advantageous to predict the influence of the medical care and/or monitoring equipment by means of simulated image data considering the positioning data of the medical care and/or monitoring equipment. Furthermore, it may be advantageously to label identified medical care and/or monitoring equipment in the simulated image and to provide the information for a later diagnosis with real obtained medical image.

According to an embodiment, the medical care and/or monitoring equipment may comprise one or more of the following a venous line, a chest tube, a tracheal tube, a nasogastric tube, an intraaortic balloon pump, and a catheter.

According to an embodiment, the at least one measuring means may comprise an optical measuring unit. The optical measuring unit may be a range camera, an optical camera, a laser, an optical sensor. The optical measuring unit may be arranged adjacent to the medical imaging system or in the medical imaging system. The optical measuring unit may be a part of the medical imaging system. The optical measuring unit may be wired (e.g. Ethernet, Profibus, etc.) and/or wireless (e.g. WIFI) connection the calculation unit. The optical measuring of the positioning data may be advantageously efficient to reliable determine the positioning data of visible areas of the subject and/or the medical care and/or monitoring equipment. The optical measuring means may advantageously be used in combination with other measuring means (e.g. pressure based measuring means) to cross check obtained positioning data.

According to an embodiment, the at least one measuring means may comprise a pressure based measuring unit, wherein the pressure based unit is arranged below the subject. The pressure based measuring unit may be a capacitive pressure sensor, an inductive pressure sensor, a hall effect based pressure sensor, or a piezo electrical pressure sensor. The pressure based measuring unit be in a wired (e.g. Ethernet, Profibus, etc.) and/or a wireless (e.g. WIFI) connection with the calculation unit. The pressure based measuring unit may be implemented below the subject in a surface of a support structure (e.g. a bed), wherein the subject lies on the support structure. In case the subject lies on the medical care and/or monitoring equipment (e.g. a venous line, a tube etc.), this is invisible but increases the pressure below the medical care and/or monitoring equipment, which is measured by the measuring unit implemented in the support structure. Hence, it is advantageously possible to identify the positioning data of invisible medical care and/or monitoring equipment.

According to an embodiment, the simulation model may further consider exposure data from the medical imaging system. The term exposure data, as used herein, is to be understood broadly and relates to setting data of the medical imaging system. The term exposure data may comprise collimator opening width, voltage value of the imaging source, positioning data of the imaging source and an imaging detector. Preferably, the exposure data may comprise a voltage value of the X-ray source. This may be advantageous to simulate accurately a resulting medical image.

According to an embodiment, the simulated image data may comprise one or more simulated X-ray images of the subject and of the at least one medical care and/or monitoring equipment, wherein the at least one medical care and/or monitoring equipment is arranged inside and/or outside the subject. This may be advantageous to assess whether the medical care and/or monitoring equipment has a negative influence on the quality of the medical image due its positioning data. This may further be advantageous to distinguish whether the medical care and/or monitoring equipment is inside and/or outside the subject.

According to an embodiment, the simulation model may further be based on a parametric anatomical model, wherein the parametric anatomical model describes a relation between one or more characteristics of a subject and a corresponding form of a body of the subject, wherein the characteristics comprise geometric characteristics and biological characteristics. The parametric anatomical model may be a generic anatomical model comprising at least a geometric model of a human body surface and a corresponding location of lungs. The parametric anatomical model may be parametrized by characteristics such as patient size, patient weight, patient BMI, lung volume, age, and/or gender. The characteristics may be measured or just inputted in the parametric anatomical model for each subject to enable an accurate modelling of the subject's individual characteristics. This may be advantageous to provide accurate feedback information, in particular an accurate simulated image.

According to an embodiment, the feedback data may further comprise guidance data configured to guide a person to adapt the positioning data and/or exposure data. The method may determine a target quality and an actual quality for the simulated image. Based on the difference between target quality and actual quality, the method may determine guidance data used to adapt positioning data and/or exposure data. The guidance data may be presented on a display to the technician. The simulation model may be trained to recognize a target quality by input of a human and/or a software assessor. The guidance data may be continuously updated when a new a simulated image is determined. For example, when a lower portion of a lung is clipped, the guidance data may comprise a graphical or textual indication that the detector should be lowered. This may be done equivalently for all other malposition directions. This may be advantageous in terms of efficiency and quality.

According to an embodiment, the method may be carried out in a preparation phase before the actual medical imaging process, and wherein the feedback data is provided during the preparation phase, and wherein the simulated image is continuously updated based on the obtained positioning data. This may be advantageous as no medical image with insufficient quality is taken and therefor radiation dose and/or unnecessary work may decrease. In other words, the simulation model allows to verify the quality of the medical image to be acquired already in the preperation phase without using the medical imaging device, i.e. radiation free. The continuously updated simulated image may enable a technologist to continuously check whether the positioning data and/or exposure data are sufficient or have to adapted. This may increase the efficiency. When the technologist adapts the subject's position or the location of the detector, e.g. an x-ray detector, the simulated image is updated accordingly. The technologist may correct the subject's position until the simulated image complies with the expected quality standards (e.g. organ is contained in the field of view, organs at risk are excluded, exterior foreign objects are not obstructing the view). Once this is achieved, the medical image, e.g. X-ray image, is acquired.

According to an embodiment, the medical system is an X-ray system and the positioning data comprise positions of the subject, an X-ray detector, an X-ray source and the medical care and/or monitoring equipment.

A further aspect relates to an apparatus for providing feedback data in a medical imaging system for a medical imaging process, comprising: a providing unit configured to provide a simulation model, trained to describe a relation between positioning data of a subject and of at least one medical care and/or monitoring equipment arranged to the subject in a medical imaging system and simulated image data resulting from the positioning data; an obtaining unit configured to obtain from at least one measuring means, positioning data of a subject and of at least one medical care and/or monitoring equipment arranged to the subject in the medical imaging system; a determining unit configured to determine feedback data by utilizing the simulation model and the obtained positioning data fed into the simulation model, wherein the feedback data comprise at least simulated image data resulting from the obtained positioning data;

a providing unit configured to provide the feedback data. The first providing unit, the second providing unit, the obtaining unit, and the determining unit may be may be each separate hardware units or implemented in one hardware unit. The hardware unit may be a CPU, a PLC, a FPGA, a microcontroller, a workstation. The first providing unit, the second providing unit, the obtaining unit, and the determining unit may also be virtual units that run on CPU, a cloud server or the like. In general the first providing unit, the second providing unit, the obtaining unit, the determining unit relate to the calculation unit.

A further aspect relates to a system, comprising: an apparatus as described above; and a medical imaging system. The medical imaging system may be an X-ray system, a MRT system, or a CT system.

A further aspect relates to a use of an optical measuring unit and/or a pressure based measuring unit in an apparatus as described above to obtain positioning data of a subject and of at least one medical care and/or monitoring equipment arranged to the subject. The optical measuring unit may be a range camera, an optical camera, a laser, an optical sensor. The pressure based measuring unit may be a capacitive pressure sensor, a inductive pressure sensor, a hall effect based pressure sensor, or a piezo electrical pressure sensor.

A last aspect relates to a computer program element, which when executed by a processor is configured to carry out the steps of the method as described above. The processor may be part of the medical imaging system, or may be provided separately in another computer device. The computer program element might be stored on a computer unit, which might also be part of an embodiment. This computing unit may be configured to perform or induce performing of the steps of the method described above. Moreover, it may be configured to operate the components of the above described device. The computing unit can be configured to operate automatically and/or to execute the orders of a user. A computer program may be loaded into a working memory of a data processor. The data processor may thus be equipped to carry out the method according to one of the preceding embodiments. This exemplary embodiment of the invention covers both, a computer program that right from the beginning uses the invention and computer program that by means of an update turns an existing program into a program that uses invention. Further on, the computer program element might be able to provide all necessary steps to fulfill the procedure of an exemplary embodiment of the method as described above. According to a further exemplary embodiment of the present invention, a computer readable medium, such as a CD-ROM, USB stick or the like, is presented wherein the computer readable medium has a computer program element stored on it which computer program element is described by the preceding section. A computer program may be stored and/or distributed on a suitable medium, such as an optical storage medium or a solid state medium supplied together with or as part of other hardware, but may also be distributed in other forms, such as via the internet or other wired or wireless telecommunication systems. However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that the above embodiments may be combined with each other irrespective of the aspect involved. Accordingly, the method may be combined with structural features of the device and/or system of the other aspects and, likewise, the device and the system may be combined with features of each other, and may also be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
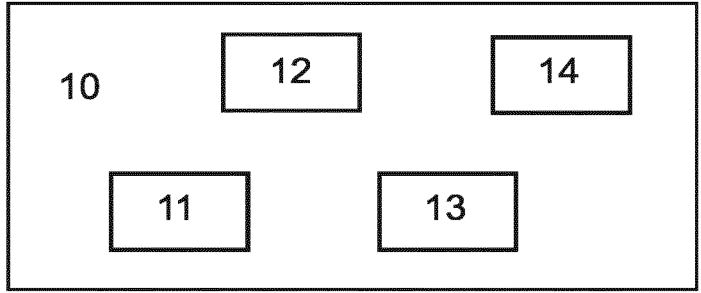
FIG. 1 shows a schematic view of an apparatus according to a first embodiment of the present disclosure.

FIG. 1 shows a schematic view of an apparatus 10 according to a first embodiment of the present disclosure. The apparatus 10 is configured for providing feedback data in a medical imaging system for a medical imaging process.

The apparatus 10 comprises a first providing unit 11 configured to provide a simulation model, trained to describe a relation between positioning data of a subject and of at least one medical care and/or monitoring equipment arranged to the subject in a medical imaging system and, optionally simulated, medical image data associated with and/or resulting from the positioning data. The simulation model may is based on a deep learning algorithm. The simulation model is trained by providing measured positioning data and machine setting data as input and corresponding actual acquired X-ray image of the subject at the same time as output. The apparatus 10 comprises further an obtaining unit 12 configured to obtain from at least one measuring means, positioning data of a subject and of at least one medical care and/or monitoring equipment arranged to the subject in the medical imaging system. The measuring means comprise an optical measuring unit and a pressure based measuring unit. In the present example, the optical measuring unit is a range camera and the pressure based measuring unit is a piezo electric pressure sensor. The range camera is arranged adjacent to the medical imaging system and the piezo electric pressure sensor is arranged in support bed wherein the subject lies on. The medical imaging system is in the present case an X-ray imaging system. The range camera and piezo electric pressure sensor are in a wired connection with the obtaining unit 12. The wired connection is an Ethernet based connection. The apparatus 10 comprises a determining unit 13 configured to determine feedback data by utilizing the simulation model and the obtained positioning data fed into the simulation model, wherein the feedback data comprise at least simulated image data resulting from the obtained positioning data. The apparatus 10 comprises further a second providing unit 14 configured to provide the feedback data. The feedback data is further transmitted to a display and displayed to a technologist preparing a subject for medical imaging. The first and second providing unit 11, 14, the obtaining unit 12, and the determining unit 13 are implemented on separate hardware units, CPUs of a workstation.

Figure 2:
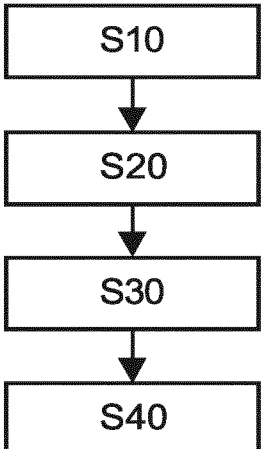
FIG. 2 shows a flow chart of a method according to a further embodiment of the present disclosure.

FIG. 2 shows a flow chart of a method according to a further embodiment of the present disclosure. The method for providing feedback in a medical imaging system for a medical imaging process comprises several steps, which do not necessarily have to be carried out in the following order.

In a first step S10 a simulation model is provided, trained to predict an appearance of a medical image to be acquired by using the medical imaging system to describe and/or from a relation between positioning data of a subject and of at least one medical care and/or monitoring equipment arranged to the subject in a medical imaging system and, optionally simulated, medical image data associated with and/or resulting from the positioning data. The simulation model is trained by providing measured positioning data, optionally machine setting data, and corresponding actual acquired X-ray image of the subject at the same time. These training data may be annotated, labelled or the like. The simulation model may be further based on a parametric anatomical model, wherein the parametric anatomical model describes a relation between one or more characteristics of a subject and a corresponding form of a body of the subject, wherein the characteristics comprise geometric characteristics and biological characteristics. The parametric anatomical model may be a generic anatomical model comprising at least a geometric model of a human body surface and a corresponding location of lungs. The parametric anatomical model may be parametrized by characteristics such as patient size, patient weight, patient BMI, lung volume, age, and/or gender. The characteristics may be measured or just inputted in the parametric anatomical model for each subject to enable an accurate modelling of the subject's individual characteristics. The simulation model may be trained to recognize a target quality by input of a human and/or a software assessor.

In a step S20, from at least one measuring means, positioning data of a subject, i.e. subject positioning data, and medical equipment positioning data of at least one medical care and/or monitoring equipment arranged to the subject in the medical imaging system are obtained. In the present example, the optical measuring unit is a optical camera, a range camera, or the like, and the pressure based measuring unit is a piezo electric pressure sensor.

In a step S30, feedback data are obtained by utilizing the simulation model and the obtained positioning data fed into the simulation model, wherein the feedback data comprise at least simulated medical image data resulting from the obtained positioning data, i.e. the current or actual subject positioning data and current or actual medical equipment positioning data.

In a step S40, the feedback data is provided. The feedback data may comprise a simulated image data. The feedback may be displayed on a display to a technologist. The feedback data may further comprise guidance data configured to guide the technologist to adapt the positioning data and/or exposure data. The method may determine a target quality and an actual quality for the simulated image. Based on the difference between target quality and actual quality the method may determine guidance data to adapt positioning data and/or exposure data. The guidance data may be displayed on a display to the technologist. The guidance data may be continuously updated when a new a simulated image is determined. For example, when a lower portion of a lung is clipped, the guidance data may comprise a graphical or textual indication that the detector should be lowered. The method may be carried out in a preparation phase before the actual medical imaging process, and wherein the feedback data is provided during the preparation phase, and wherein the simulated X-ray image is continuously updated based on the obtained positioning data.

Figure 3:
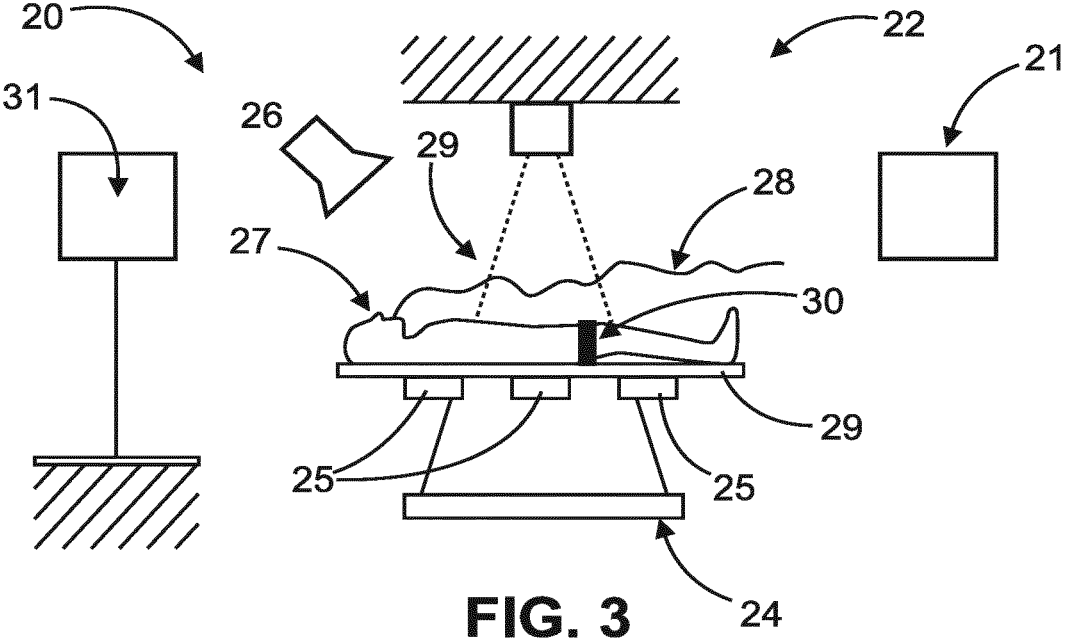
FIG. 3 shows a schematic view of a system according to a further embodiment of the present disclosure.

FIG. 3 shows a schematic view of a system 20 for a medical imaging process. The system 20 comprises an apparatus 21 as described above with reference to FIG. 1, i.e. the apparatus 10, and a medical imaging system 22, in the present case an X-ray imaging system. The X-ray imaging system 22 comprises an X-ray source 23 and an X-ray detector 24. The X-ray imaging system may be stationary or mobile (e.g. in an intensive care unit). A subject 27 is provided with a medical care and/or monitoring equipment 28, in the present example a tracheal tube. As can be seen, the medical care and/or monitoring equipment 27 is in the field of view 29 of the medical imaging system 22. Hence, the medical care and/or monitoring equipment may influence the quality of medical image as it may hide an organ or may interfere with the beam path during image acquisition due to its material and/or position relative to the subject 27 and/or the medical imaging system 22. The system 20 further comprises measuring means, in the present case a range camera 26 configured to measure the position and size of the subject 27 and of the medical care and/or monitoring equipment 28. The range camera may also detect the position of the X-ray source 23 and of the X-ray detector 24. Furthermore, the system comprises a further measuring mean, in the present case, piezo based pressure sensors 25 that are arranged below the support structure 29 (i.e. medical bed) on which the subject 27 lies. The piezo based pressure sensors measure pressure distributions. Based on the pressure distributions the apparatus 20 determines positioning data of the subject 27 and/or of the further medical care and/or monitoring equipment 30. The further medical care and/or monitoring equipment 30 is in the present case a hip guide, which assists the subjects 27 position. As the range camera can only determine the positioning data of visible areas, the piezo based pressure sensors are able to determine that the subject 27 partly lies on the hip guide 30. The measuring means 25 and 26 are in wired connection with the apparatus 21. The system 20 further comprises display 29 that displays feedback data in the form a simulated image of the X-ray image that would be acquired under the current imaging situation. The system provides continuously feedback data and guidance data to a technologist (not shown) in order to assist the technologist to adapt positioning data and/or exposure data.

In another exemplary embodiment, a computer program or computer program element is provided that is configured to execute the method steps of the method according to one of the preceding embodiments, on an appropriate device or system.

The computer program element might therefore be stored on a data processing unit, which might also be part of an embodiment. This data processing unit may be configured to perform or induce performing of the steps of the method described above. Moreover, it may be configured to operate the components of the above described device and/or system. The computing unit can be configured to operate automatically and/or to execute the orders of a user. A computer program may be loaded into a working memory of a data processor. The data processor may thus be equipped to carry out the method according to one of the preceding embodiments.

Further, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that embodiments of the present disclosure are described with reference to different subject matter. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and the foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

10, 21 apparatus
11 providing unit
12 obtaining unit
13 determining unit
14 providing unit
20 system
22 medical imaging system
23 X-ray source
24 X-ray detector
25 pressure sensor
26 range camera
27 subject
28, 30 medical equipment, e.g. medical care and/or monitoring equipment
29 field of view
31 display
S10 providing a simulation model
S20 obtaining positioning data
S30 determining feedback data
S40 providing the feedback data.

The invention claimed is:

1. A method for providing feedback data in a medical imaging system for a medical imaging process, comprising:

providing a simulation model trained to predict an appearance of a medical image to be acquired by using 1) subject positioning data associated with a captured positioning of a subject and 2) equipment positioning data associated with a captured positioning of at least one medical care and/or monitoring equipment arranged in or at the subject in the medical imaging system;

obtaining, from at least one measuring device, current subject positioning data of the subject and current equipment positioning data of the at least one medical care and/or monitoring equipment arranged in or at the subject in the medical imaging system;

determining feedback data by feeding the current subject positioning data and the current equipment positioning data into the simulation model, wherein the feedback data comprise at least simulated medical image data predicted by the simulation model from the current subject positioning data and the current equipment positioning data, wherein the simulated medical image data is continuously updated based on the current subject positioning data and the current equipment positioning data; and providing the feedback data.

2. The method according to claim 1, wherein the method is carried out in a preparation phase prior to the actual medical imaging process, and wherein the feedback data is provided in or during the preparation phase.

3. The method according to claim 1, wherein the medical care and/or monitoring equipment comprises one or more of: a venous line, a chest tube, a tracheal tube, a nasogastric tube, an intra-aortic balloon pump, and a catheter.

4. The method according to claim 1, wherein the at least one measuring device comprises an optical measuring unit configured to capture one or more images of the subject and/or the medical care and/or monitoring equipment.

5. The method according to claim 1, wherein the at least one measuring device comprises a pressure based measuring unit, wherein the pressure based unit is arranged below the subject to obtain the subject positioning data.

6. The method according to claim 1, wherein the simulation model further considers exposure data from the medical imaging system.

7. The method according to claim 1, wherein the simulated medical image data comprises one or more simulated X-ray images of the subject and of the at least one medical care and/or monitoring equipment, wherein the at least one medical care and/or monitoring equipment is arranged inside and/or outside the subject.

8. The method according to claim 1, wherein the simulation model is further based on a parametric anatomical model, wherein the parametric anatomical model describes a relation between one or more characteristics of a subject and a corresponding form of a body of the subject, wherein the characteristics comprise geometric characteristics and biological characteristics.

9. The method according to claim 1, wherein the feedback data further comprises guidance data configured to guide a person to adapt the positioning of the subject, the positioning of the medical care and/or monitoring equipment, and/or exposure data.

10. The method according to claim 1, wherein the medical system is an X-ray system, and the simulation model takes into account positions of the subject, an X-ray detector, an X-ray source and the medical care and/or monitoring equipment.

11. An apparatus for providing feedback data in a medical imaging system for a medical imaging process, comprising:

a memory that stores a plurality of instructions; and a processor coupled to the memory and configured to execute the plurality of instructions to:

provide a simulation model trained to predict an appearance of a medical image to be acquired by using 1) subject positioning data associated with a captured positioning of a subject and 2) equipment positioning data associated with a captured positioning of at least one medical care and/or monitoring equipment arranged in or at the subject in the medical imaging system;

obtain from at least one measuring device current subject positioning data of the subject and current equipment positioning data of the at least one medical care and/or monitoring equipment arranged in or at the subject in the medical imaging system;

determine feedback data by feeding the current subject positioning data and the current equipment positioning data into the simulation model, wherein the feedback data comprise at least simulated medical image data predicted by the simulation model from the current subject positioning data and the current equipment positioning data, wherein the simulated medical image data is continuously updated based on the current subject positioning data and the current equipment positioning data; and provide the feedback data.

12. A non-transitory computer readable medium for storing executable instructions, which when executed by at least one processor, cause the method according to claim 1 to be performed.

* * * * *